United States Patent [19]
Hodd

[11] Patent Number: 5,821,306
[45] Date of Patent: Oct. 13, 1998

[54] INTRAOCULAR LENS MATERIALS

[75] Inventor: Kenn Hodd, Groningen, Netherlands

[73] Assignee: Pharmacia & Upjohn Groningen BV, Groningen, Netherlands

[21] Appl. No.: 809,612

[22] PCT Filed: Oct. 6, 1995

[86] PCT No.: PCT/SE95/01152

§ 371 Date: Jun. 9, 1997

§ 102(e) Date: Jun. 9, 1997

[87] PCT Pub. No.: WO96/11235

PCT Pub. Date: Apr. 18, 1996

[30]     Foreign Application Priority Data

Oct. 6, 1994 [SE] Sweden .................................. 9403392

[51] Int. Cl.$^6$ ................................................. C08L 33/06
[52] U.S. Cl. ............................................ 525/228; 523/106
[58] Field of Search ........................... 523/106; 526/326; 525/228

[56]     References Cited

U.S. PATENT DOCUMENTS

| | | | |
|---|---|---|---|
| 4,022,754 | 5/1977 | Howes | 526/264 |
| 4,709,000 | 11/1987 | Wenzel | 526/326 |
| 5,098,803 | 3/1992 | Monroe | 430/1 |
| 5,528,322 | 6/1996 | Jinkerson | 526/312 |
| 5,532,067 | 7/1996 | Fischer | 526/326 |
| 5,618,316 | 4/1997 | Hoffman | 623/6 |

*Primary Examiner*—Paul R. Michl
*Attorney, Agent, or Firm*—Dinsmore & Shohl LLP

[57]     ABSTRACT

An intraocular lens manufactured from a homogeneous polymer blend, comprising about 70–95 weight percent of a first polymer and about 5–30 weight percent of a second polymer, wherein the first polymer comprises a poly(phenylethylacrylate) and the second polymer comprises a poly(phenylethylmethacrylate).

20 Claims, No Drawings

INTRAOCULAR LENS MATERIALS

The present invention is related to the field of intraocular lenses and especially to materials based on polyacrylate based polymers to be used in the production of deformable lenses facilitating small incision surgery procedures.

When an ophthalmic surgeon operates on an eye to remove a cataract (s)he replaces the defective natural lens with a small artificial lens. The material most commonly used for the manufacture of such intraocular lenses (IOLs) is the rigid amorphous plastic poly(methylmethacrylate) (PMMA).

In order to remove the natural lens as well as for introducing the IOL an incision into the eye has to be made. The minimum size of an incision required for a rigid lens to be implanted is about 5–6 mm. Such large incisions might give rise to various wound-related problems, including infection, wound leak and astigmatism. During the last years small incision surgery has become increasingly popular among ophthalmic surgeons. The problems indicated above are eliminated with such a technique which in addition allows less restricted early postoperative physical activity and more rapid optical rehabilitation. The phacoemulsification technique for removing the natural lens, while the major part of the capsule bag is maintained, was one essential step in the development of the small incision technique. These techniques involve implanting intraocular lenses through incision as small as about 2 mm and therefore, lenses to be used in these procedures have in common the feature of being deformable to a cross-section area small enough to match the small incision. The development of such lenses is therefore another essential step. A number of lens materials which fulfill this criteria, at least to some extent, have been suggested, for instance soft silicone materials which can be deformed, for instance folded or rolled-up, prior to insertion, and hydrogels, which are deformed and dehydrated to overall small size prior to insertion and which in contact with aqueous humor inside the eye swell to the desired size.

Whilst the advantages of elastomeric silicone IOLs is well established, these lenses have some limitations, in particular silicones have a lower refractive index than PMMA (1.49), which has been adopted as the standard for IOL materials.

A further consequence of the lower refractive index of the silicone elastomer is the requirement for a thicker lens for any given dioptre than is necessary for e.g. PMMA. This factor taken together with its high rubber elasticity, results in its rapid and powerful recovery from folding, which is undesirable in the context of its use for posterior chamber lenses.

To overcome some of these disadvantages alternative flexible lens materials have been sought which combine a high refractive index with a lower elasticity. Acrylic polymers have been favoured because of their ease of preparation, high level of atacticity - ensuring low crystallinity, good processing characteristics, high optical quality and long term stability to UV.

A typical method of producing such acrylic polymers is by copolymerisation. Thus in U.S. Pat. No. 5,290,892 (Nestle SA) is reported the preparation of copolymers of 2-phenylacrylate and 2-phenylethylmethacrylate for use in the manufacture of IOLs. These polymers have refractive indices close to 1.55, glass transition temperatures (Tg) near to 37° C. and an elongation of 200%.

I have now found that new improved materials for the preparation of intraocular lenses can be prepared from blends of certain polyacrylate-based polymers. The invention is accordingly related to the preparation of such homogenous blends with desired optical and mechanical characteristics as well as the use of such materials for the preparation of intraocular lenses.

In theory, depending on the thermodynamics of the interactions between the component polymers of a mixture and the mixing kinetics, polymer blends may be homogeneous or heterogeneous. A homogeneous blend of amorphous polymers is a single phase system which is totally transparent and has other physical properties which are intermediate between the properties of its component polymers. However, the formation of homogeneous polymer blends is a very rare phenomenon and most combinations of polymers form heterogeneous blends which are translucent or opaque. I, in accordance with the present invention have found that certain acrylate based polymers can be used for the preparation of homogeneous blends with refractive indices of 1.49 and higher. The group includes combinations of polymers having a repeating structure of the general formula

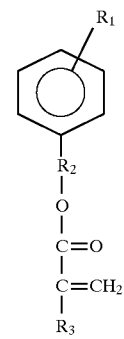

wherein R1, which is a substituent in the 1 or 2 positions, is H when R2 is ethylene, methyl when R2 is methylene or ethyl when R2 is a single bond;

R3 is hydrogen or methyl.

The materials are prepared from two or more polymers as defined above wherein at least one of the polymers in the blend, preferably that polymer which is present in the greatest proportion, containing a polyethylenically unsaturated monomer for cross-linking.

In one embodiment of the invention the blend is prepared from two polymers wherein in a first polymer $R_1$ is H, $R_2$ is ethylene and $R_3$ is H and in a second polymer $R_1$ is H, $R_2$ is ethylene and $R_3$ is methyl. The first polymer is preferably present in a concentration of about 70–90 wt%, and the other in a concentration of 10–30 wt%.

The blends are especially based on polymers of phenylethylacrylate, phenylethylmethacrylate, methylphenylacrylates and methylphenylmethacrylates. The blends specifically comprise the following combinations of polymer components:

1) poly(2-phenylethylacrylate) (2-PPEA) and poly(2-phenylethylmethacrylate) (2-PPEMA),
2) poly(1-phenylethylacrylate) (1-PPEA) and poly(2-phenylethylacrylate) (2-PPEA)
3) poly(1-phenylethylacrylate) (1-PPEA) and poly(2-phenylethylmethacrylate) (2-PPEMA)
4) poly(1-phenylethylacrylate) (1-PPEA) and poly(1-phenylethylmethacrylate) (1-PPEMA)
5) poly(2-phenylethylacrylate) (2-PPEA) and poly(1-phenylethylmethacrylate) (1-PPEMA)
6) poly(2-methylphenylacrylate) (2-PMPA) and poly(2-methylphenylmethacrylate (2-PMPMA).

The polymer combinations, and the proportion of each component, are selected such that the blends derived from them are characterized by the desirable physical properties required for foldable IOLs, and in particular a low glass transition temperature (Tg), in the interval of −10° to +37° C., especially around 30° C., an elongation greater than 100% and a high refractive index, at least 1.49, especially around 1.55 to 1.58. Thus starting with two selected homopolymers a range of transparent materials from rubbery to glassy may be readily prepared.

Optionally the blend comprises a UV absorbing component in a concentration of about 2 wt%.

Blends of poly(2-phenylethylmethacrylate) (PPEMA) and poly(2-phenylethylacrylate (PPEA) have been prepared in the range of 0–20 wt% PPEMA by latex blending and their glass transition temperatures and refractive indices measured. The glass transition temperatures were measured using a conventional differential thermal analytical technique. The refractive indices were measured at 20° C. with an Abbé refractometer. The results of these tests are shown in Table 1. It was a characteristic feature of each blend composition that only one Tg was observed, which indicates that the blend was homogeneous. Similar values for the Tgs and R.I.s were obtained for blends of PPEA and PPEMA, produced by melt blending, and blends crosslinked by ethylidene norbornene.

TABLE 1

Glass transition temperatures and refractive indices of blends of poly(2-phenylethylmethacrylate (PPEA) and poly(2-phenylethylmethacrylate) (PPEMA).

| Composition of blend | | Properties of blend | |
|---|---|---|---|
| PPEA (%) | PPEMA (%) | Tg (°C.) | R.I. |
| 95 | 5 | 17 | |
| 90 | 10 | 19 | 1.554 |
| 85 | 15 | 20 | |
| 80 | 20 | 22 | 1.557 |

In a presently preferred embodiment of the invention the blend comprises about 5.0 moles of 2-PPEA+0.5 moles of 2-PPEMA, each polymer modified by the addition of about 1.5% of a cross-linking monomer at the polymerisation step. Optionally one or more of the polymer components of the blend may in addition contain a UV-absorber of the type known from the art of intraocular lens production. The UV-absorber may be chemically bound to one or both polymer components forming the blend or being just incorporated into the final product and retained in the matrix of the cured polymer materials.

Typical crosslinking monomers include 1,4-butanedioldiacrylate, diethyleneglycol bisallylcarbonate, bisphenol A bisallylcarbonate, diallyl phthalate, resorcinol diacrylate and hydroquinone diacrylate. The crosslinking agent is preferably present in a concentration of about 0.5–5 wt%.

A number of methods of preparing polymer blends have been reported in the literature, including melt mixing and blending solutions of polymers. In the context of IOL manufacture these methods have a variety of drawbacks, for example, the removal of the final traces of a solvent from a polymer of high molecular weight may necessitate protracted procedures.

Another approach is to mix the polymers in the form of finely divided solid particles. Usually, these particles will be derived from emulsion or suspension polymerisation. The particles obtained by these processes suffer from the disadvantage that they may be contaminated, superficially, with the emulsifying or suspending agents that are added to prevent the mass of monomer coalescing during polymerisation, and such contamination is very difficult to remove, completely.

Recently the preparation of finely divided poly (methylmethacrylate) has been reported using monomer dispersed in an agarose gel (IT Patent application 67967). An advantage of this approach is that the suspension agent, the polysaccharide (agarose), is readily removed with water. This source of finely particulate polymer is employed to prepare polymer blends. The finely divided polymers, derived by gel suspension polymerisation of the individual monomers in an agarose gel, are blended mechanically.

The polymer blends, as described above, are pressed into sheets at a high temperature to effect their cure. IOLs can then be machined from the sheets. Alternatively, the polymer blends are pressed at low temperature and discs cut from them for moulding IOLs at high temperature. Either route results in IOLs of a lightly cross-linked elastomeric polymer blend.

Materials suitable for preparation of lenses according to the present invention will now be exemplified.

1. Solution blending 0.5 g of PPEMA and 4.5 g of PPEA were placed in a 250 g bottle with a screw cap and 100 ml of toluene (analytical grade) was added. The bottle was closed and shaken for 6 h or until the polymers had dissolved completely. The resulting solution of polymers was poured into a Teflon casting tray, and the toluene allowed to evaporate. When the solution had become a viscous "gel" the polymer blend was transferred to a vacuum oven and dried at 23° C. 13.3 Pa for 96 h.

The product was a coherent, transparent and tacky film, containing an homogenous blend of PPEMA (10%) and PPEA (90%).

EXAMPLE 2

Melt blending 2.1.

3.0 g of PPEMA and 27.0 g of PPEA were placed in the mixing chamber of a Brabender Plastograph and blended at 70° C. using full power for 30 minutes. The blend was discharged from the Plastograph and pressed at 70° C. into a uniform transparent sheet of the homogeneously blended PPEMA (10%) and PPEA (90%).

2.2

Powdered PPEMA and PPEA were mixed in weight ratio 5:95 and fed continuously into a 16 mm twin screw extruder with barrel temperature settings of 35°, 55° and 75° C. (increasing from hopper to die). At the die the extrudate, in the form of a lace, was water cooled to 5° C. The product was a transparent, homogeneous blend of the two polymers.

EXAMPLE 3

Latex (or Emulsion) blending 3.1

A filtered latex of PPBHA (50 ml, solids content 34 wt%, but the method is readily adapted for solids contents in the range of 20 to 40 wt%) was mixed with vigorous stirring, with a filtered latex of PPEA (950 ml, also 34 wt% solids content), the proportions required for a 5% PPEMA:95%PPEA blend. To the resulting latex was added 500 ml of methanol to precipitate the mixed polymers, and the coagulum was filtered, washed with further methanol and water and dried in vacuum oven at 40° C./13.3Pa. The homogenisation of the blend was improved by the methods of melt blending described in Example 2. above.

3.2
To a filtered latex of PPEMA (29.4 ml, solids content 34%) was added the ingredients necessary for the polymerisation of PEA as indicated in the following description:

| Deionised water or buffer solution | 200 ml |
| --- | --- |
| 2-phenylethylacrylate (inhibitor free) | 90 g |
| sodium lauryl sulphate | 1.0 g |
| ammonium persulphate | 0.3 g |

The water was charged into the reactor containing PPEMA latex and stirred at 350 rpm under nitrogen, while raising the temperature to 50° C. At this temperature, the initiator and emulsifier were added, followed by 5 wt% of PEA. The remaining 95% PEA was added at a rate of 1 ml/min, commencing 10 min later.

Heating was continued for 15 min following the completed addition of the feed, and the reaction cooled to ambient temperature. The resulting latex was filtered into methanol and the precipitated blend collected by filtration, washed with methanol and water, dried in vacuo and converted to a suitable form for moulding by one of the melt blending processes described above (Examples 2.1 and 2.2).

EXAMPLE 4

The preparation of a cross-linkable poly(2-phenylethylacrylate) for blending.

| deionised water or buffer solution | 200 ml |
| --- | --- |
| 2-phenylethylacrylate (inhibitor free) | 90 g |
| ethylidene norbornene (EN) | 5.0 g |
| sodium lauryl sulphate | 1.0 g |
| ammonium persulphate | 0.3 g |
| ferrous sulphate | 1.0 g |

The water was charged into a reactor and stirred at 350 rpm under nitrogen with the temperature at 20° C. The initiating system and emulsifier were added followed by 5 wt% of PEA. The remaining 95 wt% PEA and EN were added at a rate of 1 ml/min, commencing 10 min later.

Stirring was continued for 15 min following the completed addition of the feed, and the reaction was stopped. The resulting latex was filtered into methanol and the precipitated polymer collected by filtration, washed with methanol, dried in vacuo and converted to a suitable form for moulding by one of the melt blending processes (see examples 1 and 2 above).

EXAMPLE 5

The preparation of a cross-linkable poly(2-phenylethylmethacrylate) for blending.

| Ingredients utilized: | |
| --- | --- |
| deionised water or buffer solution | 200 ml |
| 2-phenylethylmethacrylate (inhibitor free) | 90 g |
| ethylidene norbornene (EN) | 5.0 g |
| sodium lauryl sulphate | 1.0 g |
| ammonium persulphate | 0.3 g |
| ferrous sulphate | 1.0 g |

The water was charged into a reactor and stirred at 350 rpm under nitrogen with the temperature at 20° C. The initiating system and emulsifier were added followed by 5wt% of PEMA. The remaining 95% PEMA and the EN were added at a rate of 1 ml/min, commencing 10 min later. Stirring was continued for 15 min following the completed addition of the feed, and the reaction was stopped. The resulting latex was filtered into methanol and the precipitated polymer collected by filtration washed with methanol and water dried in vacuo and converted to a suitable form for moulding by one of the melt blending processes (see examples 1 and 2)

I claim:

1. A homogeneous polymer blend, comprising about 70–95 weight percent of a first polymer and about 5–30 weight percent of a second polymer, wherein the first polymer comprises a poly(phenylethylacrylate) and the second polymer comprises a poly(phenylethylmethacrylate).

2. A blend according to claim 1, wherein the first and second polymers comprise, respectively, poly(2-phenylethylacrylate) and poly(2-phenylethylmethacrylate), poly(1-phenylethylacrylate) and poly(2-phenylethylmethacrylate), poly(1-phenylethylacrylate) and poly(1-phenylethylmethacrylate), or poly(2-phenylethylacrylate) and poly(1-phenylethylmethacrylate).

3. A blend according to claim 1, having a glass transition temperature less than 37° C., an elongation greater than 100% and a refractive index greater than 1.54.

4. A blend according to claim 1, having a refractive index greater than 1.54.

5. A blend according to claim 1, comprising about 70–90 weight percent of the first polymer and about 10–30 weight percent of the second polymer.

6. A blend according to claim 1, further comprising a UV absorber.

7. A blend according to claim 1, wherein the first and second polymers are crosslinked.

8. A blend according to claim 3, wherein the first and second polymers are crosslinked.

9. A blend according to claim 4, wherein the first and second polymers are crosslinked.

10. An intraocular lens manufactured from the homogenous polymer blend of claim 7.

11. An intraocular lens manufactured from the homogenous polymer blend of claim 8.

12. An intraocular lens manufactured from the homogenous polymer blend of claim 9.

13. A homogenous polymer blend, comprising about 70–90 weight percent of a first polymer and about 10–30 weight percent of a second polymer, wherein the first polymer comprises poly(2-methylphenylacrylate) and the second polymer comprises poly(2-methylphenylmethacrylate).

14. A blend according to claim 13, having a glass transition temperature less than 37° C., an elongation greater than 100% and a refractive index greater than 1.54.

15. A blend according to claim 13, having a refractive index greater than 1.54.

16. A blend according to claim 13, wherein the first and second polymers are crosslinked.

17. An intraocular lens manufactured from the homogenous polymer blend of claim 16.

18. A homogeneous polymer blend, comprising about 70–90 weight percent of a first polymer and about 10–30 weight percent of a second polymer, wherein the first polymer comprises poly(1-phenylethylacrylate) and the second polymer comprises poly(2-phenylethylacrylate).

19. A blend according to claim 18, wherein the first and second polymers are crosslinked.

20. An intraocular lens manufactured from the homogenous polymer blend of claim 19.

* * * * *

UNITED STATES PATENT AND TRADEMARK OFFICE
CERTIFICATE OF CORRECTION

PATENT NO. : 5,821,306
DATED : October 13, 1998
INVENTOR(S) : Kenn Hodd

It is certified that error appears in the above-identified patent and that said Letters Patent is hereby corrected as shown below:

Claim 10, bridging lines 1-2, replace "homogenous" with --homogeneous--.

Claim 11, bridging lines 1-2, replace "homogenous" with --homogeneous--.

Claim 12, bridging lines 1-2, replace "homogenous" with --homogeneous--.

Claim 13, line 1, replace "homogenous" with --homogeneous--.

Claim 17, bridging lines 1-2, replace "homogenous" with --homogeneous--.

Claim 20, bridging lines 1-2, replace "homogenous" with --homogeneous--.

Signed and Sealed this

Second Day of March, 1999

Attest:

Q. TODD DICKINSON

*Attesting Officer*  Acting Commissioner of Patents and Trademarks